(12) United States Patent
Fleming

(10) Patent No.: US 11,375,837 B2
(45) Date of Patent: Jul. 5, 2022

(54) COLLAPSIBLE FOOTWEAR TOOL

(71) Applicant: VIVE HEALTH LLC, Naples, FL (US)

(72) Inventor: Matthew Francis Fleming, Naples, FL (US)

(73) Assignee: Vive Health LLC, Naples, FL (US)

(*) Notice: Subject to any disclaimer, the term of this patent is extended or adjusted under 35 U.S.C. 154(b) by 252 days.

(21) Appl. No.: 16/526,369

(22) Filed: Jul. 30, 2019

(65) Prior Publication Data

US 2021/0030184 A1 Feb. 4, 2021

(51) Int. Cl.
*A47G 25/82* (2006.01)
*A61F 4/00* (2006.01)

(52) U.S. Cl.
CPC .............. *A47G 25/82* (2013.01); *A61F 4/00* (2013.01)

(58) Field of Classification Search
CPC ........ A47G 25/80; A47G 25/82; A47G 25/84; A47G 25/86; A47G 25/90; A47G 25/905; A47G 25/907; A47G 25/908; A61F 4/00

USPC ........ 223/111, 112, 113, 114, 115, 116, 117, 223/118, 119

See application file for complete search history.

(56) References Cited

U.S. PATENT DOCUMENTS

| 5,392,800 | A | * | 2/1995 | Sergi | A45B 3/00 |
| | | | | | 135/65 |
| 2019/0261800 | A1 | * | 8/2019 | Taylor | A47G 25/908 |
| 2019/0282011 | A1 | * | 9/2019 | Zhang | A47G 25/82 |

* cited by examiner

*Primary Examiner* — F Griffin Hall
(74) *Attorney, Agent, or Firm* — Workman Nydegger

(57) ABSTRACT

A multi-use footwear tool that has an attachment mechanism with two complementary pieces that can be separated to split the multi-use footwear tool into two sections. A first section of the multi-use footwear tool is an elongated shoehorn and a second section of the multi-use footwear tool is an elongated body. The elongated shoehorn has a shoehorn and the elongated body has a hook. The elongated shoehorn and the elongated body can be attached into one long multi-use footwear tool or separated into individual pieces using the attachment mechanism.

15 Claims, 8 Drawing Sheets

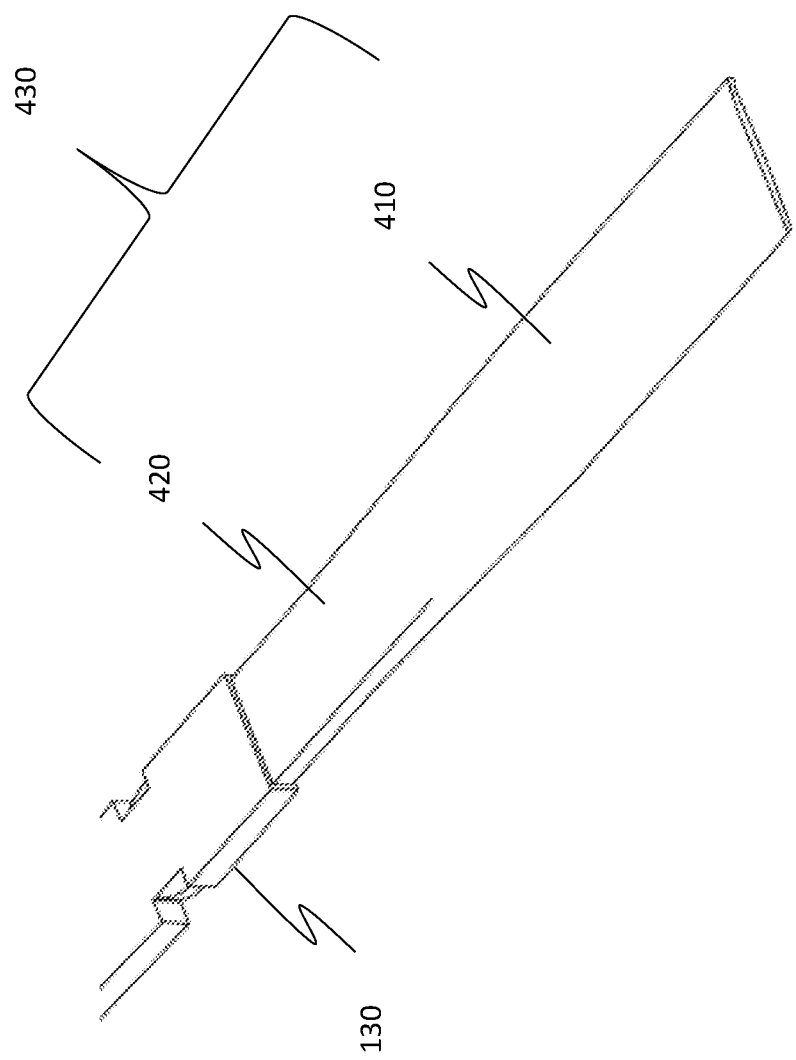

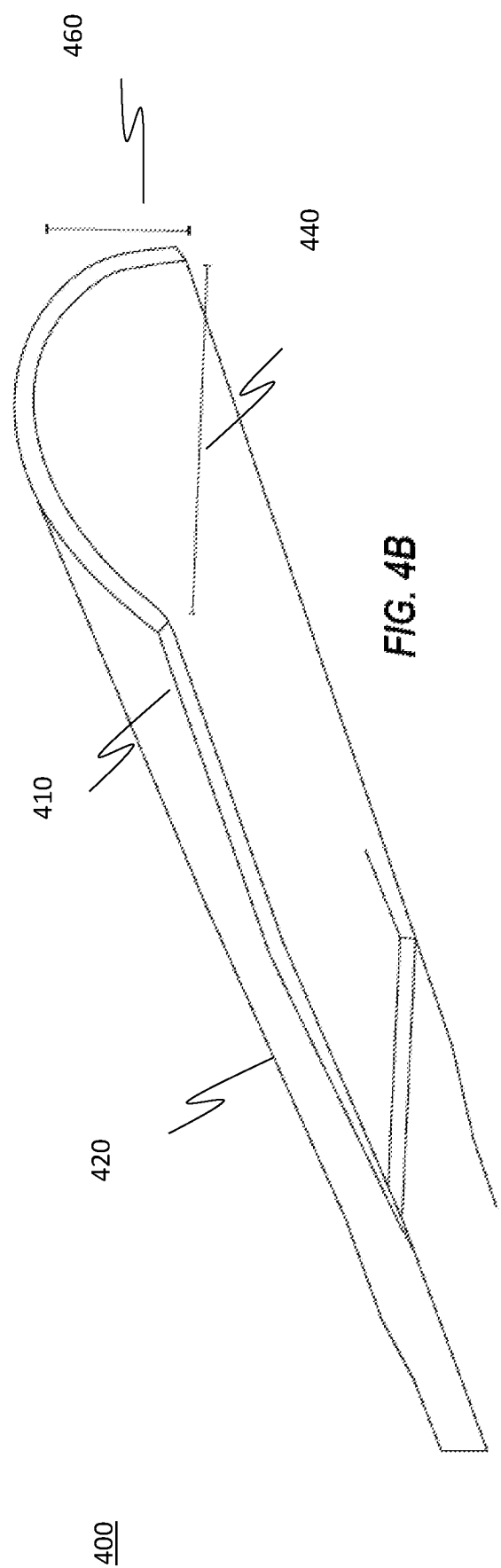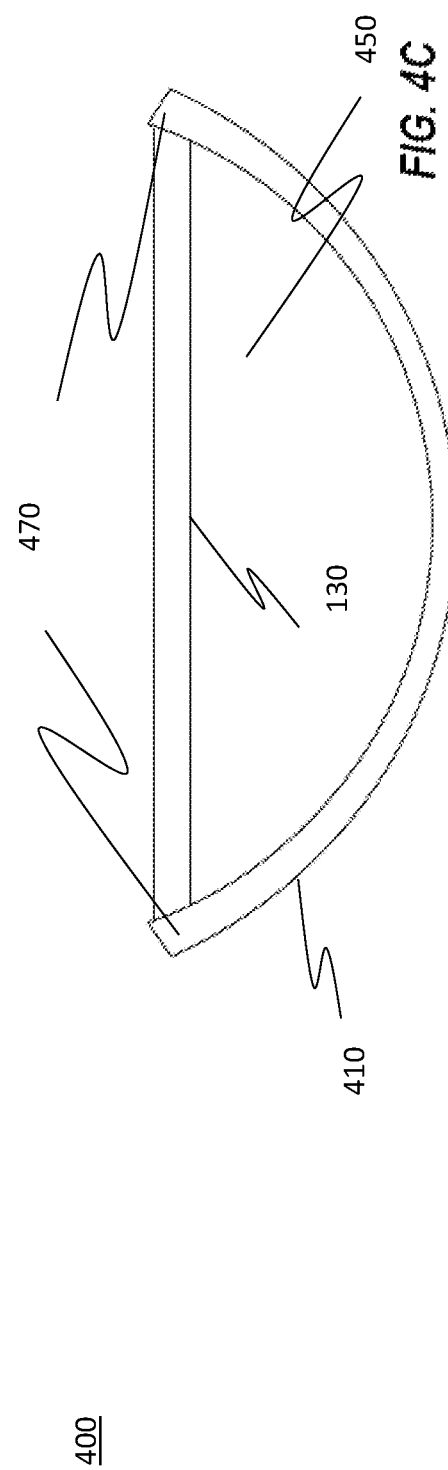

COLLAPSIBLE FOOTWEAR TOOL

BACKGROUND

Technical Field

This disclosure generally relates to consumer tools. More specifically, the present disclosure relates to tools for enabling the removal and application of footwear (i.e. socks and shoes).

Related Technology

Life expectancy and life quality of human beings have increased drastically from what they were 150 years ago. Average life expectancy in the United States has increased approximately 20 years since 1850. In that time, we have developed medicine to ease aches and pains, antibiotics to combat infections, and surgeries to keep us feeling young longer. But regardless of how far our medical procedures and tools have come, there comes a time when many humans will experience a debilitating lack of mobility.

Lack of mobility cannot always be solved by modern medicine. Today, few medical advances have been made, for example, to aid women in late stages of pregnancy in moving around and accomplishing everyday life tasks with a protruding stomach. Similarly, elderly individuals can mitigate problems with their aging joints through knee and hip replacements, but the surgical procedures can only stave off the inevitable weakening for so long. Even healthy, young individuals can experience restricted mobility from, for example, muscle tightness following a strenuous workout. In any case, muscle and joint soreness can be symptomatically treated using over the counter analgesics, but there is little that can be done to directly address the coincident restricted mobility or the wide-ranging effects that may have on the individual's daily tasks.

During these moments of incapability or decreased mobility, certain tasks that were once seemingly simple can become monumentally difficult—tasks like putting on and taking of socks and shoes. Bending down to pull on a shoe can be difficult with stiff muscles or joints or when experiencing a lack of balance affected by decreased mobility. Even sitting down while applying or removing footwear can be challenging due to mobility problems.

Accordingly, there are a number of disadvantages with removing or applying footwear that can be addressed.

BRIEF SUMMARY

Implementations of the present disclosure solve one or more of the foregoing or other problems in the art with systems, methods, and apparatuses for removing and applying footwear, such as shoes and socks. In particular, one or more implementations can include a multi-use footwear tool for removing and applying shoes and socks that has a shoehorn and a hook separable by an attachment mechanism. The multi-use footwear tool can additionally include a hinge, or multiple hinges that allow the tool to be collapsible for alternative use or convenient storage.

An exemplary multi-use footwear tool includes two distinct sides, an elongated shoehorn side having a shoehorn and an elongated body having a hook. The elongated shoehorn side can, in its entirety, be an arcuate structure with a first complementary piece attached to an end of the arcuate structure. Alternatively, the elongated shoehorn side can have a transition section adjacent to the attachment mechanism, in which the arcuate structure tapers into an angular body. When present, the angular body of the elongated shoehorn can be attached to the first piece of the attachment mechanism or to a first side of a hinge. The elongated body of the exemplary multi-use footwear tool can be coupled to a second complementary piece of the attachment mechanism (or second side of a hinge) on an end tip of the elongated body and can additionally include a hook on an end of the elongated body opposite the second complementary piece.

The hook can extend from a surface of the elongated body and protrude away from the elongated body. The hook may have two sections: a curved section and a planar section. When present, the curved section connects to the elongated body and extends in a direction away from the surface of the elongated body. The planar section is attached to a protruding end of the curved section and extends substantially parallel to the elongated body.

In one aspect, the first and second complementary pieces of the attachment mechanism can split and reattach the elongated shoehorn side and the elongated body side from one another.

In one aspect, the multi-use footwear tool can have a handle at an end tip of the elongated body, the end tip being placed on an end opposite the second complementary piece of the attachment mechanism. The handle can be configured for easier use, such as, being set as to create an obtuse angle between the handle and a surface of the multi-use footwear tool.

In one aspect, a multi-use footwear tool has multiple hinges disposed on the elongated body and/or the elongated shoehorn. The hinges can be placed as to collapse the longest surface of the tool for alternative use or convenient storage.

Accordingly, multi-use footwear tools are disclosed.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims or may be learned by the practice of the disclosure as set forth hereinafter.

BRIEF DESCRIPTION OF THE DRAWINGS

In order to describe the manner in which the above recited and other advantages and features of the disclosure can be obtained, a more particular description of the disclosure briefly described above will be rendered by reference to specific embodiments thereof, which are illustrated in the appended drawings. It is appreciated that these drawings depict only typical embodiments of the disclosure and are not therefore to be considered to be limiting of its scope.

In the drawings, multiple instances of an element may each include separate letters appended to the element number. For example, two instances of a particular element "100" may be labeled as "100*a*" and "100*b*." In that case, the element label may be used without an appended letter (e.g., "100") to generally refer to every instance of the element, while the element label will include an appended letter (e.g., "100a") to refer to a specific instance of the element. Similarly, a drawing number may include separate letters appended thereto. For example, FIG. 2 may include FIG. 2A and FIG. 2B. In that case, the drawing number may be used without the appended letter (e.g., FIG. 2) to generally refer to every instance of the drawing, while the drawing label will include an appended letter (e.g., FIG. 2A) to refer to a specific instance of the drawing. The disclosure will be described and explained with additional specificity and detail through the use of the accompanying drawings in which:

FIG. 4A illustrates a rear perspective view of the shoehorn side of the exemplary multi-use footwear tool of FIGS. 1A and 1B.

FIG. 4B illustrates a front bottom perspective view of the shoehorn side of the multi-use footwear tool illustrated in FIG. 4A.

FIG. 4C illustrates an end view of the shoehorn side of the multi-use footwear tool illustrated in FIGS. 4A and 4B.

DETAILED DESCRIPTION

Figure 1A:
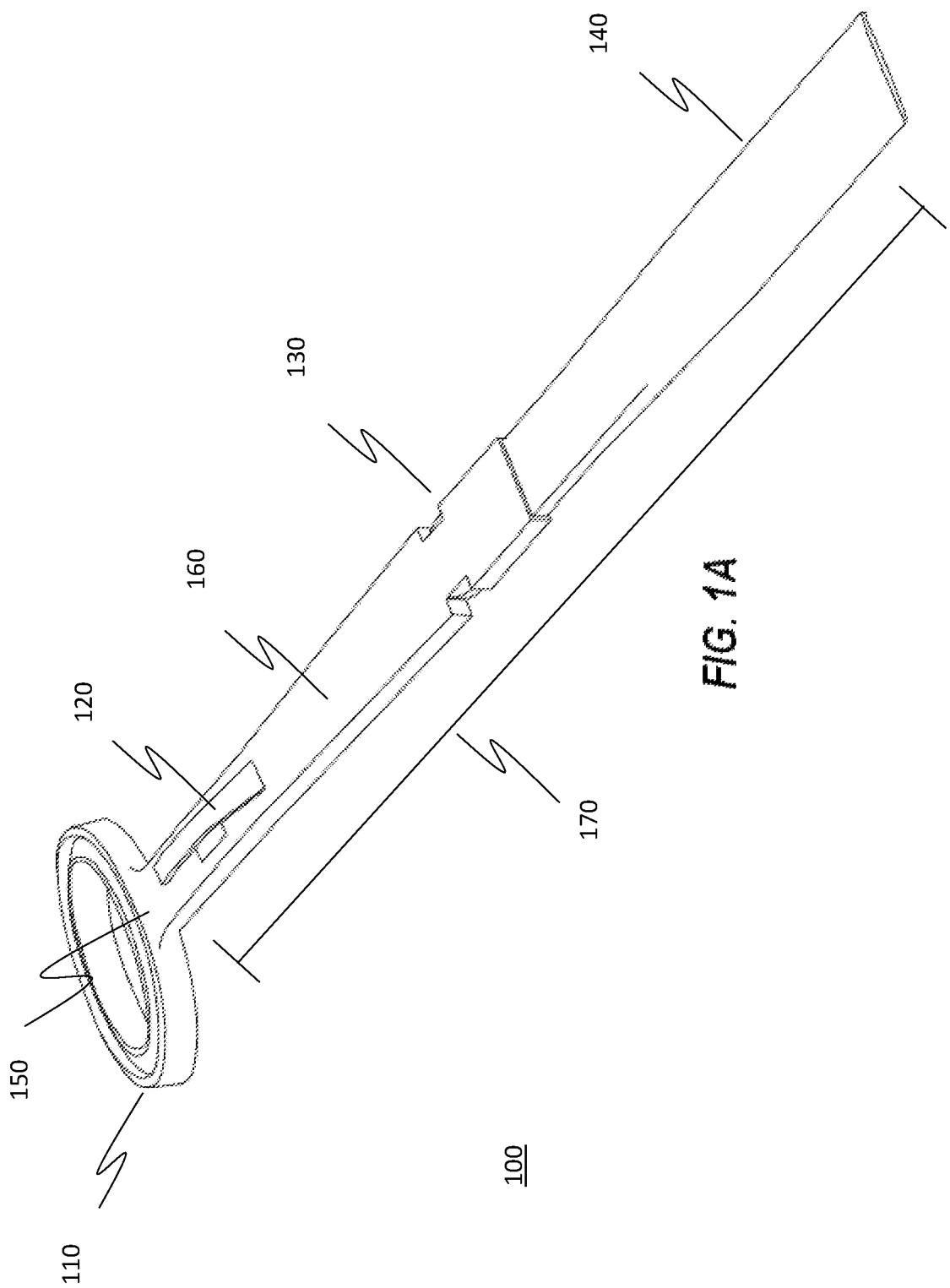
FIG. 1A illustrates a front perspective view of a multi-use footwear tool, according to one or more embodiment of the present disclosure.

Before describing various embodiments of the present disclosure in detail, it is to be understood that this disclosure is not limited to the parameters of the particularly exemplified systems, methods, apparatus, products, processes, and/or kits, which may, of course, vary. Thus, while certain embodiments of the present disclosure will be described in detail, with reference to specific configurations, parameters, components, elements, etc., the descriptions are illustrative and are not to be construed as limiting the scope of the claimed invention. In addition, the terminology used herein is for the purpose of describing the embodiments and is not necessarily intended to limit the scope of the claimed invention.

Furthermore, it is understood that for any given component or embodiment described herein, any of the possible candidates or alternatives listed for that component may generally be used individually or in combination with one another, unless implicitly or explicitly understood or stated otherwise. Additionally, it will be understood that any list of such candidates or alternatives is merely illustrative, not limiting, unless implicitly or explicitly understood or stated otherwise.

In addition, unless otherwise indicated, numbers expressing quantities, constituents, distances, or other measurements used in the specification and claims are to be understood as being modified by the term "about," as that term is defined herein. Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

Any headings and subheadings used herein are for organizational purposes only and are not meant to be used to limit the scope of the description or the claims.

Overview of Multi-Use Footwear Tools

As briefly discussed above, a lack of mobility can affect anyone. It can be caused by a number of circumstances, such as weakness, stiffness, or pain, and can negatively impact the everyday lives of affected individuals. During these moments of incapability or lack of mobility, certain tasks that seem simple on a normal, healthy day, may instead be monumentally difficult. Tasks like putting on shoes. Bending down to pull on a shoe is difficult with stiff muscles or joints or a lack of balance caused by reduced mobility. Even sitting down while applying or removing a shoe can be challenging or impossible due to mobility problems.

Embodiments of the present disclosure enable the removal and application of footwear. A multi-use footwear tool as described herein can include a hook that can be used for sock removal and a shoehorn for manipulating shoes—combined in a single extended length tool that can be used while standing. The multi-use footwear tools described herein solve one or more problems in the art of removing and applying footwear. Advantageously, the tools disclosed herein are long enough to aid those suffering from a lack of mobility, while being collapsible for ease of storage and increased portability. Additionally, the multi-use footwear tool can be adaptable for alternative use to enable operation in a variety of ways to further assist those struggling with stiffness or other mobility issues thereby enabling an individual to more easily navigate and accomplish their everyday tasks, particularly donning and doffing footwear.

Abbreviated List of Defined Terms

To assist in understanding the scope and content of the foregoing and forthcoming written description and appended claims, a select few terms are defined directly below.

The term "attachment mechanism," as used herein, includes any device in one or more pieces that may be used to "attach" two or more components or to "attach" one component to another component. The term "attach" and/or "attachment" may refer to its common dictionary definition where appropriate, but it may contextually refer to particular acts of connecting, associating, affixing, fastening, sticking, joining, or any combination of the foregoing that cause an object to be fixedly or selectively proximate another object. In some embodiments, the attachment mechanism may be an integral part of a component, whereas in other embodiments, the attachment mechanism may be separate.

An attachment mechanism is to be understood to have any number of movable and/or fixed parts, any of which may be singularly or in combination with one or more components interact to facilitate attachment. As non-limiting examples, an attachment mechanism may include a mechanism for attaching components using one or more—or a combination of—chemical adhesives (e.g., an epoxy and/or other thermosetting adhesives, glue, cement, paste, tape and/or other pressure-sensitive adhesives, etc.), mechanical fasteners (e.g., threaded fasteners such as a combination of a threaded rod together with a complementary threaded nut, rivets, screws, clamps, buckles, tenon and mortise pairs, hook and loop fasteners, dual lock reclosable fasteners, cable ties, rubber bands, etc.), magnets, vacuums (e.g., suction cups, etc.), and/or interference fittings (e.g., press fittings, friction fittings, etc.). Additionally, or alternatively, an attachment mechanism may include any material or element resulting from physically attaching two or more components by crimping, welding, and/or soldering.

The term "end tip," as used herein is intended to be understood as a face of the multi-use footwear tool that is perpendicular to a longest surface of the multi-use footwear tool.

The term "longest surface," as used herein is intended to be understood as a distance on a surface of the multi-use footwear tool from a distal end to an opposite distal end, that exceeds any other distance of a surface of the multi-use footwear tool The term "multi-use footwear tool" is sometimes used interchangeably herein, as a "tool" and/or "footwear tool."

The term "elongated shoehorn" is sometimes used interchangeably herein, as a "shoehorn side."

The term "elongated body" is sometimes used interchangeably herein, as a "hook side."

Unless defined otherwise, all technical and scientific terms used herein have the same meaning as commonly understood by one of ordinary skill in the art to which the present disclosure pertains.

Various aspects of the present disclosure, including devices, systems, and methods may be illustrated with reference to one or more embodiments or implementations, which are exemplary in nature. As used herein, the term "exemplary" means "serving as an example, instance, or illustration," and should not necessarily be construed as preferred or advantageous over other embodiments disclosed herein. In addition, reference to an "implementation" of the present disclosure or invention includes a specific reference to one or more embodiments thereof, and vice versa, and is intended to provide illustrative examples without limiting the scope of the invention, which is indicated by the appended claims rather than by the following description.

As used throughout this application the words "can" and "may" are used in a permissive sense (i.e., meaning having the potential to), rather than the mandatory sense (i.e., meaning must). Additionally, the terms "including," "having," "involving," "containing," "characterized by," as well as variants thereof (e.g., "includes," "has," "involves," "contains," etc.), and similar terms as used herein, including within the claims, shall be inclusive and/or open-ended, shall have the same meaning as the word "comprising" and variants thereof (e.g., "comprise" and "comprises"), and do not exclude additional un-recited elements or method steps, illustratively.

It will be noted that, as used in this specification and the appended claims, the singular forms "a," "an" and "the" include plural referents unless the context clearly dictates otherwise. Thus, for example, reference to a singular referent (e.g., "widget") includes one, two, or more referents. Similarly, reference to a plurality of referents should be interpreted as comprising a single referent and/or a plurality of referents unless the content and/or context clearly dictate otherwise. For example, reference to referents in the plural form (e.g., "widgets") does not necessarily require a plurality of such referents. Instead, it will be appreciated that independent of the inferred number of referents, one or more referents are contemplated herein unless stated otherwise.

As used herein, directional terms, such as "top," "bottom," "left," "right," "up," "down," "upper," "lower," "proximal," "distal" and the like are used herein solely to indicate relative directions and are not otherwise intended to limit the scope of the disclosure and/or claimed invention.

To facilitate understanding, like reference numerals (i.e., like numbering of components and/or elements) have been used, where possible, to designate like elements common to the figures. Specifically, in the exemplary embodiments illustrated in the figures, like structures, or structures with like functions, will be provided with similar reference designations, where possible. Specific language will be used herein to describe the exemplary embodiments. Nevertheless, it will be understood that no limitation of the scope of the disclosure is thereby intended. Rather, it is to be understood that the language used to describe the exemplary embodiments is illustrative only and is not to be construed as limiting the scope of the disclosure (unless such language is expressly described herein as essential).

Any headings used herein are for organizational purposes only and are not meant to be used to limit the scope of the description or the claims.

Various aspects of the present disclosure can be illustrated by describing components that are bound, coupled, attached, connected, and/or joined together. As used herein, the terms "bound," "coupled", "attached", "connected," and/or "joined" are used to indicate either a direct association between two components or, where appropriate, an indirect association with one another through intervening or intermediate components. In contrast, when a component is referred to as being "directly bound," "directly coupled", "directly attached", "directly connected," and/or "directly joined" to another component, no intervening elements are present or contemplated. Furthermore, binding, coupling, attaching, connecting, and/or joining can comprise mechanical and/or chemical association.

Although the subject matter described herein is provided in language specific to structural features and/or methodological acts, it is to be understood that the subject matter defined in the appended claims is not necessarily limited to the described features or acts so described. Rather, the described features and acts are disclosed as example forms of implementing the claims.

Multi-Use Footwear Tool

The multi-use footwear tools described herein can be used as an accessibility tool to assist users in removing and/or applying footwear, particularly socks and shoes. The disclosed embodiments are particularly useful for individuals who may have difficulty completing such tasks without aid.

Figure 1B:
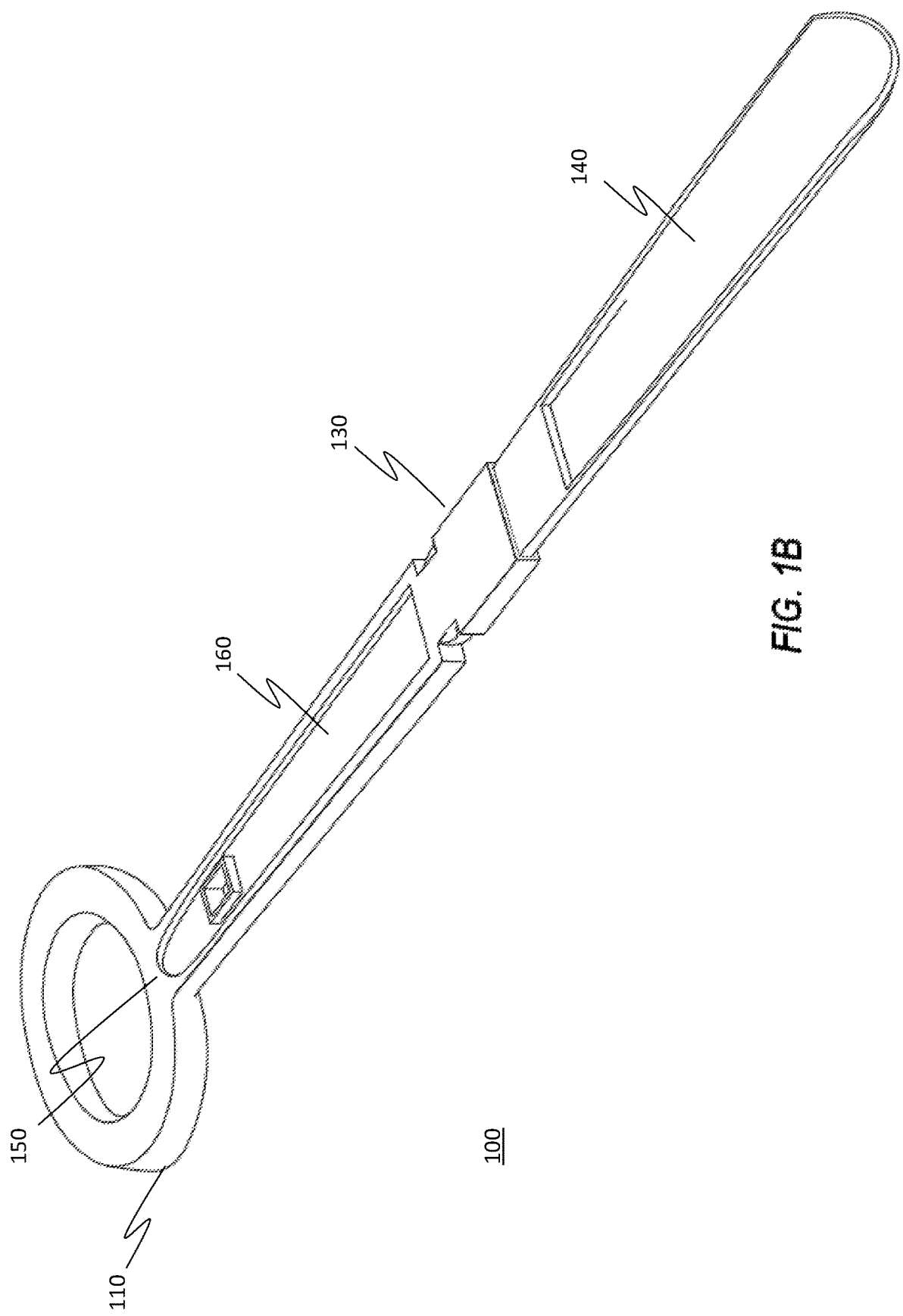
FIG. 1B illustrates a rear perspective view of the multi-use footwear tool of FIG. 1A, according to one or more embodiment of the present disclosure.

An exemplary multi-use footwear tool 100 of the present disclosure is illustrated in FIGS. 1A and 1B. FIG. 1A illustrates a bottom side view of the tool 100 and FIG. 1B illustrates the same tool 100 of FIG. 1A but from a top side view.

As shown, the multi-use footwear tool 100 includes apparatuses to facilitate the removal and application of footwear, such as a hook 120 and shoehorn 140. The tool can advantageously be configured to separate into individual pieces for alternative or individual use and/or efficient storage. When assembled, the tool 100 can be, in some embodiments, between one and three feet long, preferably between 1.5 and 2.5 feet long, which is a desirable length that enables users to implement the tool at a distance as an aid for their decreased mobility. Such length is also beneficial for able-bodied users to more efficiently don and doff footwear. For example, if an individual is standing and needs to remove a shoe, the individual can use the long tool to remove the shoe with the shoehorn without needing to bend down. Additionally, the tool can also be used for removing a sock with the hook from a distance. Further, the tool can be separated, and the individual pieces can be used in closer proximity. For example, if a user wishes to put on a shoe while sitting down, the shoehorn can aid in the donning of the shoe without the unnecessary length of the full tool that could be too cumbersome for the given application.

Additional details of an embodiment for a multi-use footwear tool 100 are illustrated in FIG. 1A. In the illustrated embodiment, the hook 120, is positioned on one side of the footwear tool 100 and protrudes away from the surface of its resident side. More specifically, the illustrated hook 120 is positioned on the elongated body 160 of the footwear tool 100 and protrudes away from the surface of the elongated body 160 forming a concave curvature with respect to the surface of the elongated body 160. The hook 120 can be sized and shaped, for example, to engage and remove a sock from a user's foot.

With continued reference to FIGS. 1A and 1B, the depicted multi-use footwear tool 100 also includes an end tip 150. The end tip 150 of the footwear tool 100 is a face of the footwear device that is perpendicular to a longest surface 170 of the multi-use footwear tool 100. The longest surface 170 of the footwear tool 100 stretches in the direction of the longitudinal axis of the tool 100 from the distal end comprising the shoehorn 140 and through the elongated body 160. As shown in FIGS. 1A and 1B, a handle 110 of the multi-use footwear tool 100 is attached to or formed integrally with the end tip 150. This positioning of the handle 110 allows increased ease of using the shoehorn 140 to remove or put on a shoe. When manipulating a shoe, the handle can provide a convenient grip that enables a user to more deftly manipulate and apply the appropriate amount of pressure (e.g., in the correct direction) with the shoehorn and thereby accomplish the designated task.

Further, the handle 110 may be angled with respect to the elongated body 160. As shown, the handle 110 can have a distal end pitched away from the planar elongated body 160, which in some embodiments can improve the handling and operation of the tool 100, particularly the shoehorn 140. The ring shape of the handle can also beneficially allow the tool to be hung, for example, on a doorknob or hanger (e.g., near an exit and/or within a closet where the user is likely to put on and/or remove footwear). In some embodiments, the angle of the handle with respect to the elongated body 160 can further enable the longitudinal axis of the tool 100 to be oriented substantially orthogonal to the ground when the crook of a hanger is passed through the handle and the tool is hung via the hanger. The ring-shaped handle 110 can additionally provide the user with multiple different gripping areas to increase ease of operability and comfort when manipulating the tool 100. Although shown as a ring, it should be appreciated that the handle 110 may have other shapes or contours. For example, the handle can be ergonomically shaped to more comfortably fit the grip. As an additional example, the handle may be bar-shaped, similar to a cane.

Figure 2:
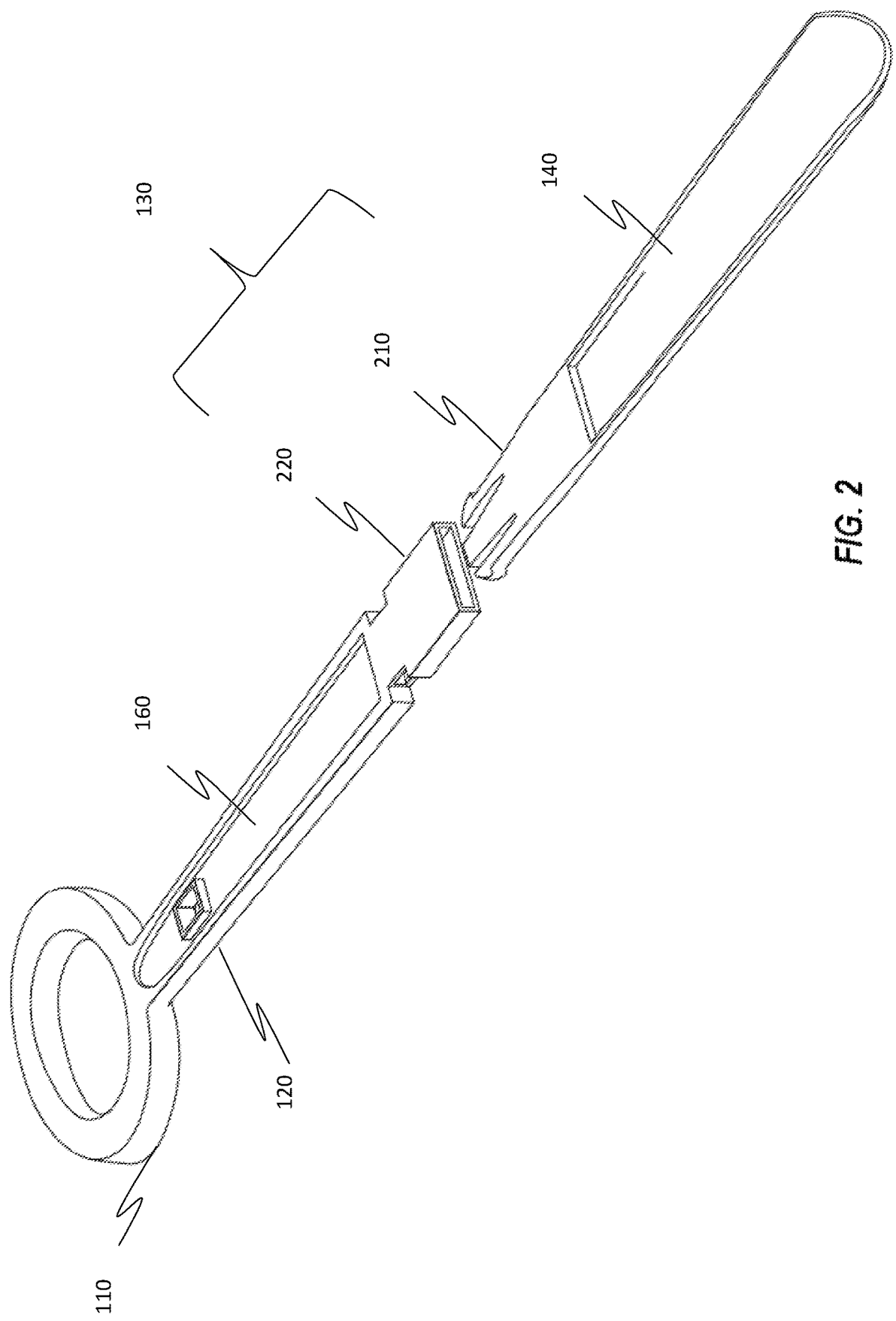
FIG. 2 illustrates the multi-use footwear tool of FIGS. 1A and 1B shown separated by the detachment of the attachment mechanism, according to one or more embodiment of the present disclosure.

The multi-use footwear tool 100 additionally includes an attachment mechanism 130 positioned between and connecting the shoehorn 140 and the elongated body 160. As shown in FIG. 2, the attachment mechanism 130, illustrated as a quick release clasp, can separate the tool 100 into two distinct pieces with the shoehorn 140 as one piece and the hook 120 and elongated body 160 as a second piece. In this way, the attachment mechanism 130 makes the tool 100 collapsible and thereby makes it easier to store and transport.

Further, by enabling the separation of the tool via the attachment mechanism 130, the individual pieces (e.g., the shoehorn and the elongated body having the hook) can be utilized for more individualized needs or instances. Removing the elongated body 160 from the shoehorn 140 allows the shoehorn 140 to be maneuvered more agilely and can be an aid to a user in more or different situations (e.g., when sitting). For example, if a user wants to remove a shoe while sitting in a chair, the long multi-use footwear tool 100 may be cumbersome to operate. The separated shoehorn 140 can allow more maneuverability for the desired use.

Likewise, when the elongated body 160 is separated from the shoehorn 140 using the attachment mechanism 130, the hook 120 (located on the opposite side of the elongated body) can be utilized to aid the user in more or different situations. Without the added length of the shoehorn 140, for example, the hook 120 may be used for situations where a shorter tool could be helpful, such as for fine motor movements of grasping and removing a sock in a seated position.

In some embodiments, the multi-use footwear tool 100 can be further configured with a secondary attachment mechanism, such as a hook and loop fasteners, snap fittings, etc., disposed along the tool and operable to secure the stacked pieces for storage. For example, a first portion of a hook and loop fastening system can be placed on the elongated body side of the tool, and a complimentary portion of the hook and loop fastening system can be placed on the shoehorn side of the tool. When the tool is decoupled and the now separated pieces are prepared for storage, the complementary hook and loop fasteners can be used to secure the stacked shoehorn and elongated body sides of the tool together, thereby reducing the likelihood the pieces will be inadvertently separated and/or lost during storage.

Rather than the first and second pieces of the attachment mechanism being disposed on the shoehorn and elongated body directly, other configurations of a multi-use footwear tool may include an elongated central body that contains the entire attachment mechanism. For example, the elongated central body can be configured to have a shoehorn attached to one end and an elongated body and hook attached to an opposite end of the elongated central body from the shoehorn. In this way, the tool can be modular and more easily fit to the height, size, ability, or preference of the user. As an illustration of the foregoing, if the intended user is six feet tall, the elongated central body can be elongated to make the multi-use footwear tool long enough to be optimally (or more comfortably) used based on the individual's height (e.g., 2.5-3 feet long). Alternatively, if the intended user is a child or smaller adult, the elongated central body may be shortened as to make tool short enough to be used effectively (or more comfortably) used by such and individual (e.g., 1.5-2 feet long). The elongate central body can be further configured with an attachment mechanism 130 disposed at a midpoint of the elongated central body.

Figure 3A:
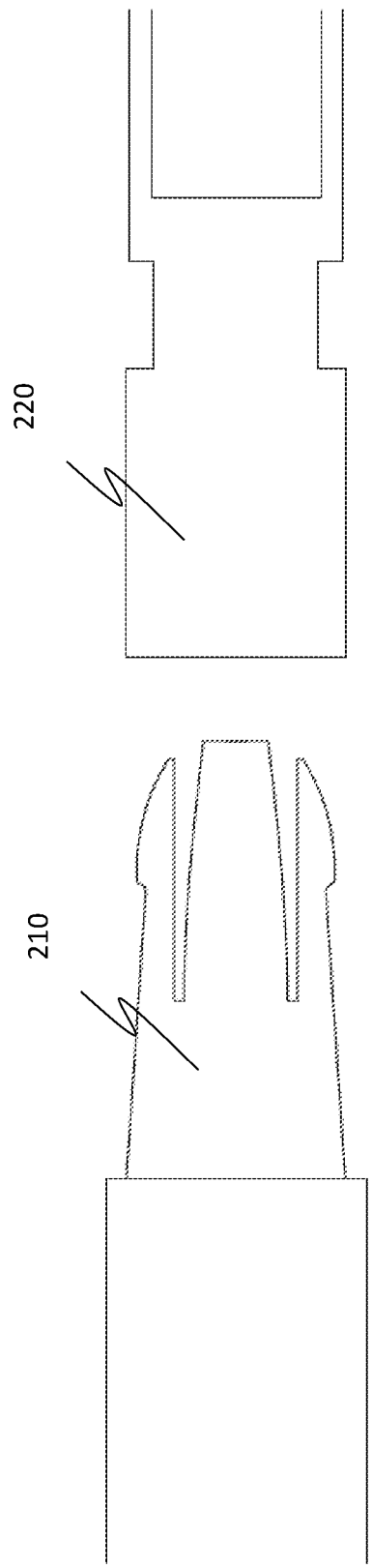
FIG. 3A illustrates a close-up view of an exemplary attachment mechanism shown in a separated configuration.
Figure 3B:
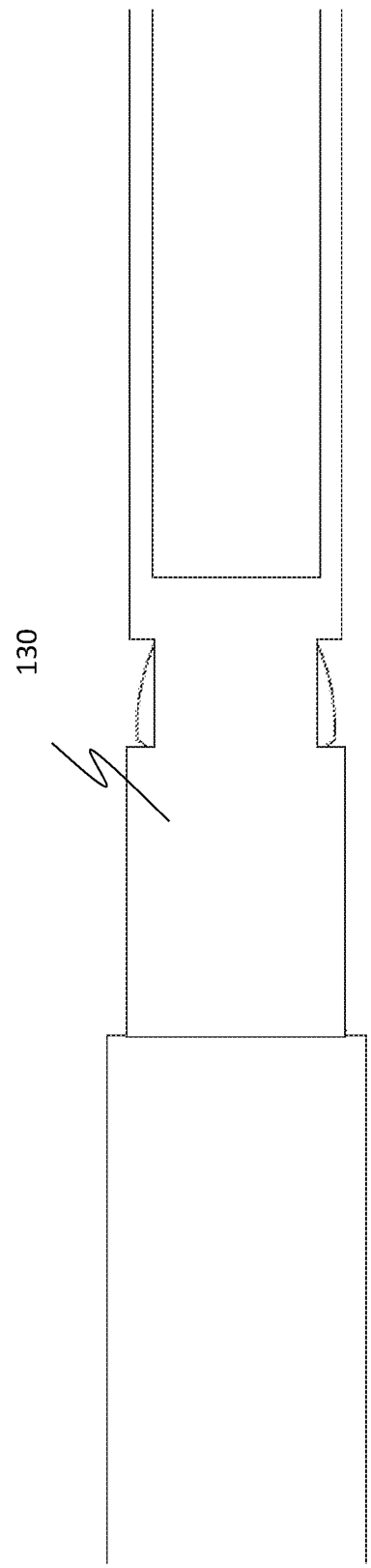
FIG. 3B illustrates a close-up of the exemplary attachment mechanism of FIG. 3A shown in a connected configuration.

The attachment mechanism 130 is illustrated in a close-up view in FIG. 3A. In some embodiments, the attachment mechanism 130 can be configured as a quick release buckle as illustrated. The quick release buckle is configured as two pieces: the first complimentary piece 210 modeled as a male buckle piece and the second complimentary piece 220 modeled as a female buckle piece. When the attachment mechanism 130 is connected, as illustrated in FIG. 3B, the first complimentary piece is inserted into the second complimentary piece. When using the multi-use footwear tool 100 in FIG. 1A as a complete device, the attachment mechanism 130 can lock into place to ensure connectivity remains consistent or secure during use.

Although illustrated as a quick-release clip in FIGS. 1A and 1B, it should be appreciated that the attachment mechanism is not intended to be so limited. The attachment mechanism can be any other attachment mechanism, as that term is defined herein, having a first complimentary piece connected/coupled to the shoehorn and a second complimentary piece connected/coupled to the elongated body that can be joined to maintain association of the shoehorn and elongated body and selectively decoupled to disassemble or collapse the tool. For example, the attachment mechanism can be spring buttons and corresponding holes in one embodiment of the present disclosure. The spring buttons can be disposed on one side of the multi-use footwear tool so they can be pressed flush with a surface from which they protrude. A side of the device with the spring buttons can be inserted inside another side of the tool that is configured with holes so that the buttons can be released to extend through the holes, locking the sides together. Alternatively, the attachment mechanism could also be straps integrally connected to one side of the tool and connectable to the other side via snaps, buttons, magnets, etc.

Attention is now directed to the shoehorn 400 of FIGS. 4A-4C. The distal end of the shoehorn is principally shaped to increase the ease by which a user can don and doff footwear. Accordingly, the arcuate structure 410 at the distal end of the shoehorn can be configured in size and shape to curve around a heel of a user's foot. In an exemplary use, the shoehorn can be slid into the back of a shoe and around the back of the heel until the distal edge securely rests within the shoe and/or against the sole of the shoe. The shoehorn then acts as a stabilizer to hold the shoe down so the foot can be removed from the shoe with increased ease. Alternatively, the shoehorn can be used to support the back of an unworn shoe and thereby keep the back or mouth of the shoe open and/or spread to more easily accept a user's foot when donning the shoe.

In some embodiments, the shoehorn 400, can include a transition section 430 disposed adjacent to the attachment section and/or between the distal end of the shoehorn and the associated portion of the attachment mechanism at the proximal end thereof. In this transition section 430, a change in the contour and/or shape of the shoehorn occurs with an arcuate structure 410 of the shoehorn 400 being disposed at the distal end of the shoehorn 400 and tapering or otherwise transforming into an angular body 420 confluent with the complementary portion of the attachment mechanism (e.g., prismatic, as shown in FIG. 4A).

Further up the shoehorn 400, where footwear is unlikely to touch, the shoehorn may not need to maintain a shape suitable for assisting a heel/foot into and/or out of footwear. Instead, a portion of the shoehorn may be used more primarily as structural support for the shoehorn/tool and/or increase the ease of manufacturing. For instance, a portion of the shoehorn may take a shape not as easily fitted around a heel and into the back of a shoe, but which may impart structural support, like the angular body 420 shown in FIGS. 4A-4C. The tapering of the shoehorn 400 from the arcuate structure 410 to the angular body 420, can allow for a more seamless connection to the attachment mechanism 130 while still maintaining enough space on the shoehorn 400 configured to remove a shoe in a potentially preferable manner.

It should be appreciated that although FIGS. 4A and 4B illustrate the shoehorn transitioning from an arcuate shape at the distal end to an angular body adjacent to the attachment mechanism, in some embodiments, the concave portion and the attachment mechanism could be connected by a planar body, arcuate body, or prismatic body. In some embodiments, the concavity of the distal end can be lengthened as to extend the entire length from the distal end to the attachment mechanism.

A close-up of a distal end of the shoehorn 400 is illustrated in FIG. 4B. In some embodiments, the shoehorn 400, may have an arcuate structure 410 defined as an arclength of a portion of a circle or ellipse constructed to match the curvature of an average human heel or the curvature of a shoe. Accordingly, in some embodiments, the arcuate structure can be defined as an arclength of an ellipse having an arcuate structure height 460 corresponding to the radius of the minor axis of the ellipse and the arcuate structure width 440 corresponding to the radius of the major axis of the ellipse. In FIG. 4B, the arcuate structure height 460 and arcuate structure width 440 are specified for the distal end of the shoehorn. In an exemplary embodiment, the arcuate structure height 460 is between 0.25-1.5 inches and the arcuate structure width 440 is between 2-4 inches.

In some instances, the curvature of the arcuate structure can be changed by adjusting the major and minor axes of the ellipse, which will affect the narrowness and shape of the concavity of the shoehorn. For example, adjusting the minor axis can account for a snugger fit. Alternatively, the major axis can be made larger, which would tend to cause the shoehorn (and thereby the mouth of the shoes applied thereto) to open more widely and more easily receive the foot of a user having a wider heel. It should be appreciated that the curvature of the shoehorn can be adapted according to the shape and/or contour desired by the user. For example, the curvature does not have to be representative of the arclength of an ellipse. In some embodiments, the curvature of the shoehorn is represented as the arclength of a circle. In this way, adjusting the radius of the circle defining the arclength of the shoehorn curvature changes the fit of the shoehorn. In some embodiments, the shoehorn represents a wide v-shaped fusion of two planar pieces and/or a wide v-shaped bend in a single planar piece.

It may be beneficial to adjust the arcuate structure height 460 and the arcuate structure width 440 to fit an intended user. For example, if a multi-use footwear tool 100 is made to fit children, the arcuate structure height 460 and the arcuate structure width 440 may need to be made smaller to fit around a child size foot. That is, the minor and major axis radii need to be decreased to better serve the user. Because of the modular nature of the disclosed tools, different sized shoehorns can also be swapped to better fit the user.

Additional aspects of the shoehorn 400 are illustrated in FIG. 4C where the distal edge of the shoehorn is viewed end on and down the shoehorn 400 to the fastener interface 450 of the attachment mechanism 130. As discussed above, the attachment mechanism 130 can be configured as a quick release buckle with a fastener interface 450 that is shaped as an angular body. Additionally, the arcuate structure 410 can be configured as a concave, hollow arc. When the arcuate structure 410 meets up with the attachment mechanism 130 (e.g., via an angular body 420, as shown in FIG. 4B), the angular body 420 may connect to the attachment mechanism 130 on less than all sides of the fastener interface 450.

In some embodiments, the arcuate structure 410 does not extend past the edges of the attachment mechanism 130. In particular, the arcuate structure edges 470, may not extend past the attachment mechanism 130. When the arcuate structure edges 470 do not extend past the attachment mechanism 130, the device can rest flat against a planar surface which can help with storing the device.

Although not depicted in FIG. 4C, it can be appreciated that the angular body of FIG. 4B could be filled, so that as the arcuate structure tapers into the angular body, it becomes a solid angular body that aligns completely with the fastener interface of the attachment mechanism. In this alternative embodiment, the solid angular body could strengthen the shoehorn 400 and make the multi-use footwear tool 100 more secure.

Figure 5:
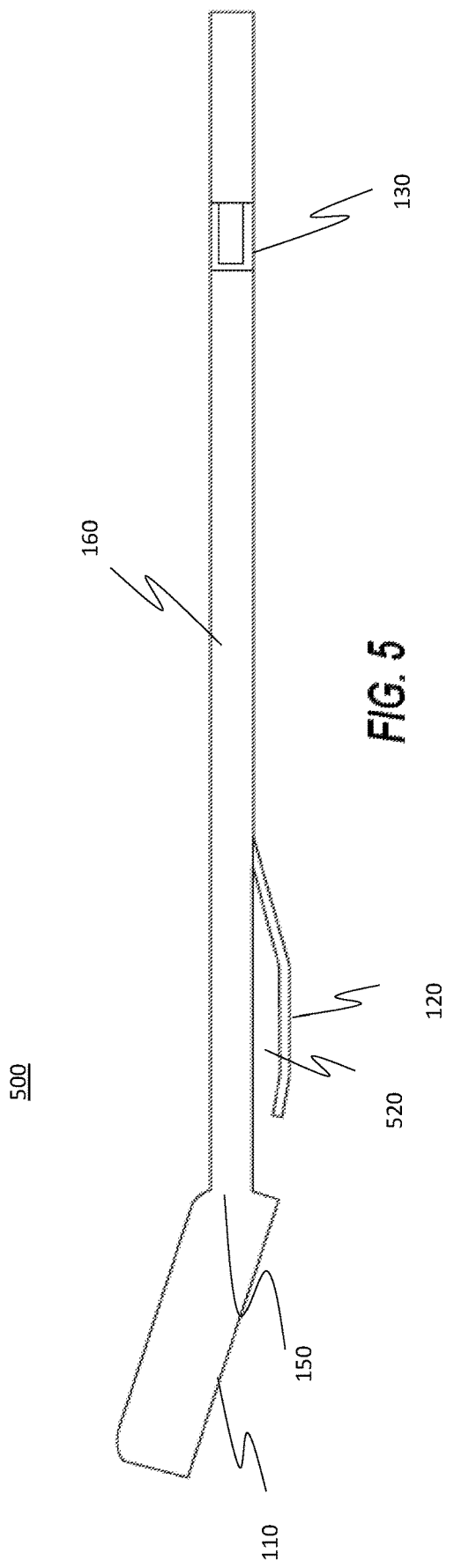
FIG. 5 illustrates a side view of the multi-use footwear tool of FIGS. 1A and 1B, depicting an elongated body of the multi-use footwear tool.

As illustrated in FIG. 5, the multi-use footwear tool 100 also includes the elongated body 160, handle 110 and hook 120 of a hook side 500. In some embodiments, the elongated body 160 extends from the attachment mechanism 130 and terminates at the end tip 150. The end tip 150 of the elongated body 160 is a surface face of the elongated body 160 which is perpendicular to a longest surface 170 of the elongated body 160.

In some embodiments, the hook side 500 protrudes away from the longest surface 170 of the elongated body 160. The hook can protrude towards the end tip 150 and over a space 520 created between the elongated body 160 and the hook 120.

The illustrated embodiment of FIG. 5 can be further configured for the hook 120 to be used as efficiently as possible. In such an exemplary use, the leading end of the hook 120 can be slid between the fabric of a worn sock and the wearer's foot until an edge of the sock abuts an inner junction between the hook 120 and the elongated body 160. Continued movement of the footwear tool 100 in a direction toward the heel and/or bottom of the wearer's foot can act to guide the sock off of the foot.

One way to accomplish the exemplary use, as stated above, is to configure the hook 120 to have two sections. In some embodiments, the hook 120 can have a curved portion which is attached to the elongated body 160 and protrudes in an outward direction, and a planar portion that is attached to an end of the curved portion. The planar portion is situated to extend substantially parallel to the elongated body 160. The benefit of the hook 120 configured with the two sections is so a user can more easily slide the hook 120 inside a sock, between the sock and a foot. By creating a relatively planar section of the hook 120, an end of the hook 120 can slide along the ankle and foot into the sock without potentially complicated maneuvering to separate the sock from the foot that you could experience with a hook 120 that is curved completely.

Additional exemplary configurations of the hook could include, in some embodiments, situating the hook 120 so it does not extend all the way from a location where the hook protrudes from the elongated body 160 to the end tip 150. When the hook 120 is a distance away from the end tip 150 and the handle 110, it can be easier to slide the hook 120 into a sock without the handle 110 or elongated body 160 getting in the way.

Further, in some embodiments of exemplary use, the hook 120 is closer to the end tip than the attachment mechanism 130. If the hook is too close to the attachment mechanism 130, a fair portion of the elongated body 160 extends from the attachment mechanism 130 and past the hook 120 and can make use of the tool more difficult.

In some embodiments, the handle 110 is attached to the elongated body 160 at the end tip 150 and extend outward away from the hook side 500. The handle 110, as stated above, can have other features, such as a tilt or a ring shape, to offer the user more control over the multi-use footwear tool 100 during use.

Alternatively, the handle can be used as a portion of a base structure for the multi-use footwear tool in some alternative embodiments. The multi-use footwear tool can be configured as a handle with a long handle shaft extending from a surface of the handle. The handle and the long handle shaft can be a main body to which additional components can be anchored. A shoehorn can be disposed on a distal end of the long handle shaft to give the advantages stated above for removal and application of footwear. Additionally, a hook can protrude from a surface of the long handle shaft for footwear manipulation.

The long handle shaft with the attached hook and shoehorn can be, in some embodiments, between 1.5 and 2.5 feet long to be utilized for standing use of the multi-use footwear tool. Additional components disclosed such as an attachment mechanism or a hinge, can be disposed at a midpoint of the long handle shaft to create a further adjustable and/or collapsible device.

Figure 6:
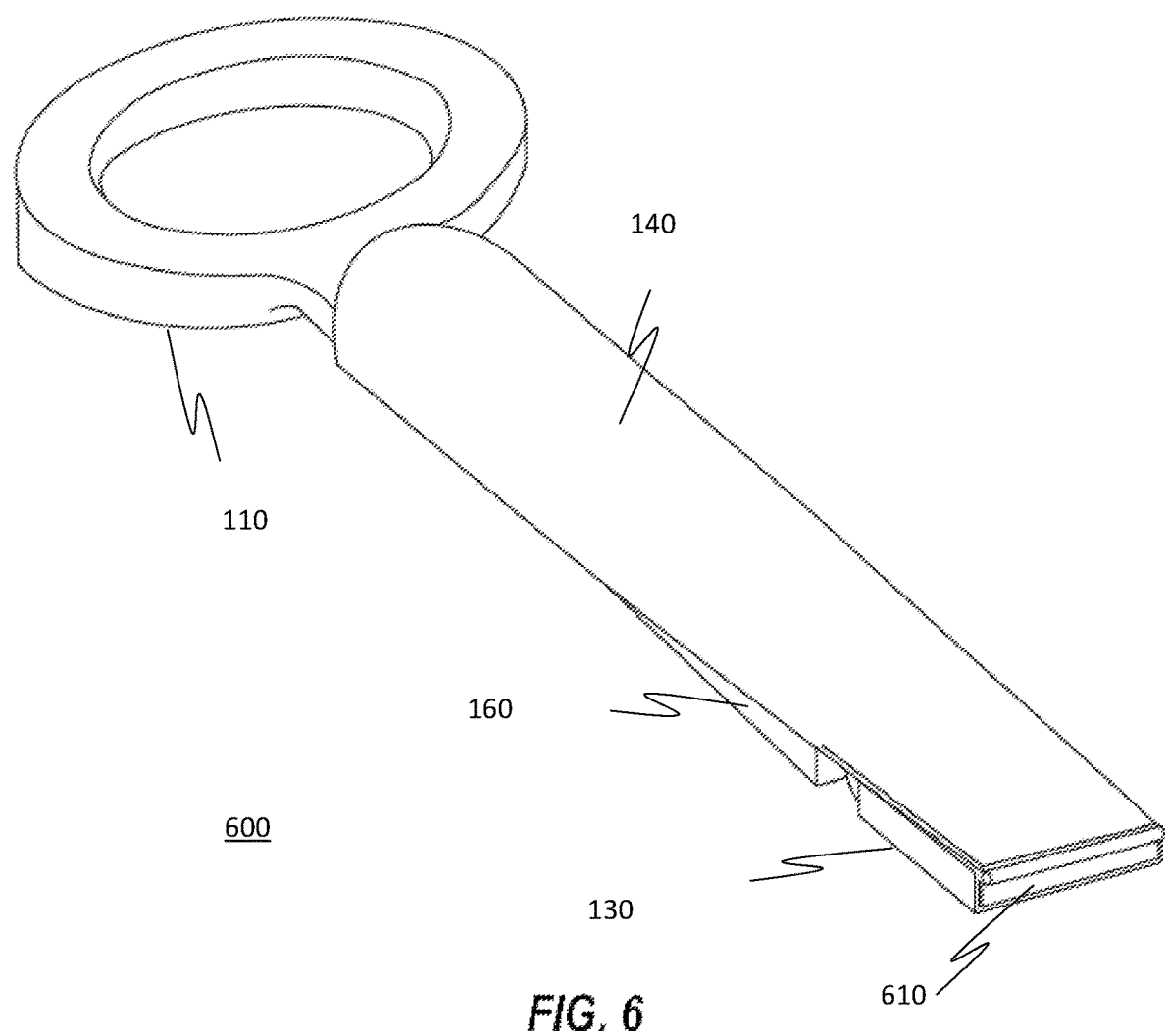
FIG. 6 illustrates a foldable multi-use footwear tool in accordance with one or more embodiments of the present disclosure.

The multi-use footwear tools described herein can be further configured with a hinge. FIG. 6 illustrates a collapsible and/or foldable multi-use footwear tool 600. The illustrated tool 600 is a multi-use footwear tool 100 with the hinge 610 disposed at a midpoint/center on the shoehorn 140 adjacent to/beside the attachment mechanism 130. The hinge 610 allows for the foldable multi-use footwear tool to be folded in half, making storage easier. Additionally, by folding the tool 600 rather than (or in addition to) separating the pieces that can be created by the attachment mechanism 130, the tool 600 can be stored in a similar amount of space as the separated pieces, while ensuring the pieces stay together. While the hinge 610 is beneficial for storing, the attachment mechanism 130 can still allow modified use of the foldable multi-use footwear tool 600 as discussed above.

In some embodiments, the shoehorn 140 is configured to fit around the outside of the elongated body 160 when the device is folded, collapsing the foldable multi-use footwear tool 600 further than if the shoehorn 140 were to sit on top of the elongated body 160.

In some embodiments, the foldable multi-use footwear tool 600, includes two hinges 610 to enable the tool 600 to have a tri-fold action, effectively splitting the multi-use footwear tool 600 into three sections. The tri-fold action can lessen the length of the space needed to house the tool 600. Alternatively, the two hinges 610 could fold like an accordion to collapse the tool 600.

In some embodiments, the hinge 610 is configured with a locking mechanism to ensure the hinge does not bend during use of the tool 600.

Conclusion

Various alterations and/or modifications of the inventive features illustrated herein, and additional applications of the principles illustrated herein, which would occur to one skilled in the relevant art and having possession of this disclosure, can be made to the illustrated embodiments without departing from the spirit and scope of the invention as defined by the claims, and are to be considered within the scope of this disclosure. Thus, while various aspects and embodiments have been disclosed herein, other aspects and embodiments are contemplated. While a number of methods and components similar or equivalent to those described herein can be used to practice embodiments of the present disclosure, only certain components and methods are described herein.

It will also be appreciated that systems, devices, products, kits, methods, and/or processes, according to certain embodiments of the present disclosure may include, incorporate, or otherwise comprise properties, features (e.g., components, members, elements, parts, and/or portions) described in other embodiments disclosed and/or described herein. Accordingly, the various features of certain embodiments can be compatible with, combined with, included in, and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include said features, members, elements, parts, and/or portions without necessarily departing from the scope of the present disclosure.

Moreover, unless a feature is described as requiring another feature in combination therewith, any feature herein may be combined with any other feature of a same or different embodiment disclosed herein. Furthermore, various well-known aspects of illustrative systems, methods, apparatus, and the like are not described herein in particular detail in order to avoid obscuring aspects of the example embodiments. Such aspects are, however, also contemplated herein.

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached disclosure for purposes of illustrating embodiments of the present disclosure, it will be apparent to those skilled in the art that various changes in the methods, products, devices, and apparatus disclosed herein may be made without departing from the scope of the disclosure or of the invention, which is defined in the appended claims. All changes which come within the meaning and range of equivalency of the claims are to be embraced within their scope.

What is claimed is:

1. A multi-use footwear tool for removing and applying footwear, comprising:
    an attachment mechanism comprising first and second complementary pieces, wherein the first and second complementary pieces are selectively separable;
    an elongated shoehorn coupled to the first complementary piece of the attachment mechanism, the elongated shoehorn comprising:
        a transition section adjacent to the attachment mechanism; and
        an arcuate structure extending from a distal end of the elongated shoehorn to the transition section, wherein the arcuate structure tapers into an angular body within the transition section;
        a hinge disposed between the attachment mechanism and the distal end of the elongated shoehorn, positioned beside the attachment mechanism; and
    an elongated body coupled to the second complementary piece of the attachment mechanism, the elongated body defining a hook on an end of the elongated body opposite the second complementary piece, wherein the hook protrudes outward from the elongated body and extends in a direction that is opposite the elongated shoehorn when the first and second complementary pieces are selectively attached, the hook creating and extending over a space between the elongated body and the hook, the hook being configured to facilitate sock removal.

2. The multi-use footwear tool as in claim 1, wherein a concavity of the hook is disposed towards the elongated body.

3. The multi-use footwear tool as in claim 2, wherein the concavity of the hook further comprises:
    a curved portion attached to the elongated body and extending away from the elongated body; and
    a planar portion attached to a distal end of the curved portion and that is substantially parallel to the elongated body.

4. The multi-use footwear tool as in claim 3, wherein a handle is disposed on an end tip of the elongated body on an end opposite the end containing the second complementary piece of the attachment mechanism.

5. The multi-use footwear tool as in claim 1, wherein a handle is disposed on an end tip of the elongated body on the end opposite the end that contains the second complementary piece of the attachment mechanism.

6. The multi-use footwear tool as in claim 1, wherein a concavity of the hook is disposed towards the elongated body, but does not extend to an end tip of the elongated body.

7. The multi-use footwear tool as in claim 6, wherein the concavity of the hook further comprises:
    a curved portion attached to the elongated body and extending away from the elongated body; and
    a planar portion attached to a distal end of the curved portion and substantially parallel to the elongated body.

8. The multi-use footwear tool as in claim 7, wherein a handle is disposed on an end tip of the elongated body on the end opposite the end which contains the second complementary piece of the attachment mechanism, forming an obtuse angle between the handle and a surface of the multi-use footwear tool.

9. The multi-use footwear tool as in claim 1, wherein the hook defines an opening between the hook and the elongated body, the opening being oriented away from the elongated shoehorn when the first and second complementary pieces are selectively attached.

10. A multi-use footwear tool for removing and applying footwear, comprising:
    an elongated central body comprising:
        a shoehorn side of the elongated central body comprising:
            an arcuate structure disposed at an end of the elongated central body; and
            a hinge;
        a hook side of the elongated central body comprising:
            a hook; and
            a space defined by the hook side of the elongated central body, wherein the hook protrudes outward from a surface of the hook side and extends in a direction that is opposite the arcuate structure, the hook extending over the space defined by the hook side between the hook and the surface of the hook side, the hook being configured to facilitate sock removal;
        a handle disposed at an end tip of the hook side of the elongated central body; and an attachment mechanism disposed at a midpoint of the elongated central body disposed adjacent to the hinge, the attachment mechanism comprising a first complementary piece coupled to the shoehorn side and a second complementary piece coupled to the hook side, wherein the first and second complementary pieces are selectively separable.

11. The multi-use footwear tool as in claim 10, wherein the hook side further comprises a handle disposed at an end tip of the elongated central body opposite the arcuate structure, forming an obtuse angle between the handle and a surface of the multi-use footwear tool.

12. A multi-use footwear tool for removing and applying footwear, comprising:
   a long handle of a length between one and three feet, the long handle comprising:
      a long handle shaft;
      a handle attached to a distal end of the long handle shaft;
      a shoehorn disposed at a distal end opposite the distal end of the handle of the long handle shaft as an arcuate structure;
      a hook that protrudes away from a surface of the long handle shaft and extends in a direction that is opposite the arcuate structure, the hook being configured to facilitate sock removal; and
      a space defined by the long handle shaft, wherein the hook protrudes outward from the long handle shaft and over the space defined by the long handle shaft between the hook and the surface of the long handle shaft, wherein a concavity of the hook is disposed towards the surface of the long handle shaft.

13. The multi-use footwear tool as in claim 12, wherein the concavity of the hook further comprises: a curved portion attached to the long handle shaft and extending away from the long handle shaft; and a planar portion attached to a distal end of the curved portion and substantially parallel to the long handle shaft.

14. The multi-use footwear tool as in claim 13, wherein there is a hinge disposed on the long handle shaft.

15. The multi-use footwear tool as in claim 14, further comprising an attachment mechanism disposed adjacent to the hinge between the hinge and the handle, the attachment mechanism comprising:
   a first complementary piece coupled to a side of the long handle that contains the shoehorn; and
   a second complementary piece coupled to a side of the long handle that contains the hook, wherein the first and second complementary pieces are selectively separable.

\* \* \* \* \*